United States Patent [19]

Shiokawa et al.

[11] Patent Number: 4,914,113
[45] Date of Patent: Apr. 3, 1990

[54] INSECTICIDAL IMIDAZOLINES

[75] Inventors: Kozo Shiokawa, Kanagawa; Shinichi Tsuboi, Tokyo; Shoko Sasaki, Tokyo; Koichi Moriya, Tokyo; Yumi Hattori, Tokyo; Katsuhiko Shibuya, Tokyo, all of Japan

[73] Assignee: Nihon Tokushu Noyaku Seizo K.K., Tokyo, Japan

[21] Appl. No.: 265,642

[22] Filed: Nov. 1, 1988

[30] Foreign Application Priority Data

Nov. 6, 1987 [JP] Japan ................... 62-279042

[51] Int. Cl.$^4$ ............... A01N 43/50; C07D 401/14; C07D 401/06
[52] U.S. Cl. ............................ 514/333; 514/341; 514/365; 514/369; 546/256; 546/278; 548/180; 548/189; 548/202; 548/205
[58] Field of Search ............... 546/278, 256; 548/202, 548/186, 205, 189; 514/333, 341, 365, 369

[56] References Cited

FOREIGN PATENT DOCUMENTS

| 0154178 | 9/1985 | European Pat. Off. |
| 0163855 | 12/1985 | European Pat. Off. |
| 0212600 | 3/1987 | European Pat. Off. |
| 0259738 | 3/1988 | European Pat. Off. |
| 0277317 | 8/1988 | European Pat. Off. |
| 2205745 | 8/1973 | Fed. Rep. of Germany |

OTHER PUBLICATIONS

F. Ishikawa, et al., *Chem. & Pharmaceutical Bulletin*, vol. 26, No. 12, Dec. 1978, pp. 3658–3665.
A. Kosasayama, et al., *Chem. & Pharmaceutical Bulletin*, vol. 27, No. 4, Apr. 1979,. pp. 841–847.

*Primary Examiner*—Richard A. Schwartz
*Attorney, Agent, or Firm*—Sprung Horn Kramer & Woods

[57] ABSTRACT

The present invention relates to novel imidazolines of the formula (I)

$$W-\underset{\underset{R}{|}}{CH}-N\underset{\underset{N-Y}{\|}}{\diagup\!\!\!=\!\!\!\diagdown}N-Z \qquad (I)$$

to processes for their production and to their use as very potent insecticides.

In formula (I) above

R represents hydrogen or alkyl,

Y represents nitro or cyano,

W represents an optinally substituted 5- or 6-membered group having at least one hetero-atom selected from the group consisting of nitrogen, oxygen and sulfur atoms, and Z represents alkyl, alkenyl, alkynyl, alkoxyalkyl, alkylthioalkyl, cyanoalkyl, haloalkenyl, aralkyl, acyl or —CH$_2$—W (wherein W has the meaning stated above).

8 Claims, No Drawings

INSECTICIDAL IMIDAZOLINES

The present invention relates to novel imidazolines, to several processes for their preparation, and to their use as insecticides.

It has already been disclosed that certain 1-substituted 1,2-dihydro-2-nitro-iminopyridines have anti-inflammatory actions (see J. Med. Chem., vol. 14, pp. 988–990 (1971)).

There have been found novel imidazolines of the formula (I)

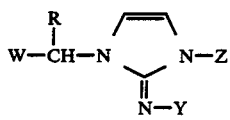     (I)

wherein
R represents hydrogen or alkyl,
Y represents nitro or cyano,
W represents an optionally substituted 5- or 6-membered heterocyclic group having at least one heteroatom selected from the group consisting of nitrogen, oxygen and sulfur atoms, and
Z represents alkyl, alkenyl, alkynyl, alkoxyalkyl, alkylthioalkyl, cyanoalkyl, haloalkenyl, aralkyl, acyl or —CH$_2$—W (wherein W has the meaning stated above).

Imidazolines of the formula (I) are obtained when
(a) compounds of the formula (II)

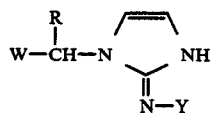     (II)

wherein R, Y and W have the meanings stated above, are reacted with compounds of the formula (III)

Z—M     (III)

wherein
Z has the meaning stated above,
M represents halogen or —OSO$_2$—L, and
L represents methyl, phenyl or tolyl.
in the presence of inert solvents, and if appropriate in the presence of bases, or
(b) compounds of the formula (IV)

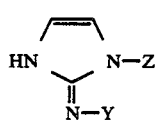     (IV)

wherein Y and Z have the meanings stated above, are reacted with compounds of the formula (V)

     (V)

wherein R, W and M have the meanings stated above, in the presence of inert solvents, and if appropriate in the presence of bases.

The novel imidazolines exhibit powerful insecticidal properties. Surprisingly, the imidazolines according to the invention exhibit a substantially greater insecticidal action than those known from the aforementioned prior art.

Among the imidazolines according to the invention, of the formula (I), preferred compounds are those wherein
R is hydrogen or methyl,
Y is nitro,
W is a 5- or 6-membered heterocyclic group having 1 or 2 heteroatoms selected from the group consisting of nitrogen, oxygen and sulfur atoms, with the proviso that at least one of the heteroatoms is nitrogen, and the heterocyclic group may optionally have at least one substituent selected from the group consisting of halogen, alkyl with 1 to 4 carbon atoms, alkoxy with 1 to 4 carbon atoms, haloalkyl with 1 to 4 carbon atoms, haloalkoxy with 1 to 4 carbon atoms, alkenyl with 2 to 4 carbon atoms, alkylthio with 1 to 4 carbon atoms, alkylsulfinyl with 1 to 4 carbon atoms, alkylsulfonyl with 1 to 4 carbon atoms, and alkynyl with 3 to 4 carbon atoms, and
Z is alkyl with 1 to 4 carbon atoms, alkenyl with 3 carbon atoms, alkynyl with 3 carbon atoms, alkoxyalkyl with 2 to 4 carbon atoms in total, alkylthioalkyl with 2 to 4 carbon atoms in total, cyano-substituted alkyl with 1 to 2 carbon atoms, chloroalkenyl with 3 carbon atoms, benzyl (which may optionally be substituted with chlorine or cyano), acetyl (which may optionally be substituted with chlorine), benzoyl or —CH$_2$—W (wherein W has the meaning stated above).

Very particularly preferred imidazolines of the formula (I) are those
wherein
R is hydrogen,
Y is nitro,
W is pyridyl or thiazolyl optionally substituted with chlorine, methyl or trifluoromethyl on the ring, and
Z is methyl, allyl, propargyl, 3-cyanobenzyl, 4-chlorobenzyl, acetyl, benzoyl, 2-chloro-5-pyridyl or 2-chloro-5-thiazolyl.

In the process (a), if, for example, 3H-1-(2-chloropyridin-5-yl-methyl)-2-nitroiminoimidazoline and methyl iodide are used as starting materials, the course of the reaction can be represented by the following equation:

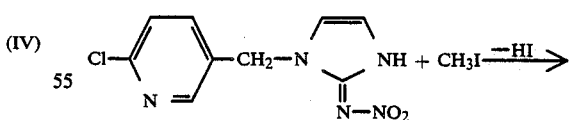

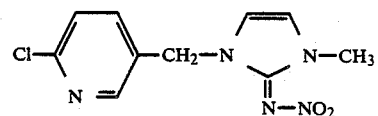

In the process (b), if, for example, 3H-1-(3-cyanobenzyl)-2-nitroiminoimidazoline and 2-chloro-5-(chloromethyl)pyridine are used as starting materials, the course of the reaction can be represented by the following equation:

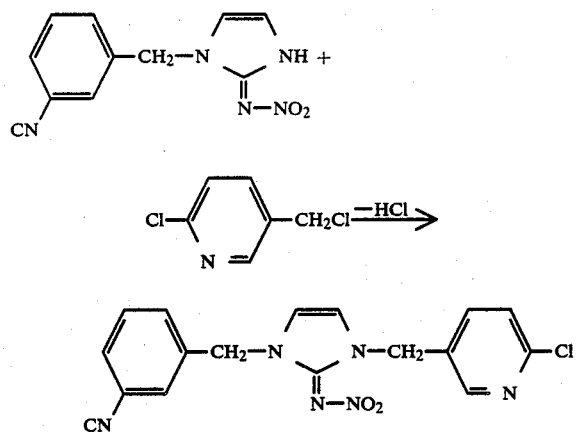

In the process (a), the compounds of the formula (II) mean compounds based on the above definitions of R, Y and W, preferrably compounds based on the above preferred definitions.

The compounds of the formula (II) are novel, and can be obtained, in general, when 2-nitroaminoimidazole of the formula

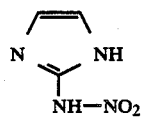

are reacted with the aforementioned compounds of the formula (V), in the presence of inert solvents.

2-nitroaminoimidazole can be obtained, as shown in an example hereinbelow, when known S-methyl-N-nitro-isothiourea is reacted with aminoacetaldehyde dimethylacetal in the presence of inert solvents.

In the process (a), the compounds of the formula (III) mean compounds based on the above definitions of Z and M.

In formula (III), Z preferably has the meanings already given above and M preferably means chlorine, bromine, iodine or tosyloxy.

The compounds of the formula (III) are already known in the field of organic chemistry, and as examples thereof there may be mentioned:
methyl iodide,
3-cyano-benzyl chloroide,
2-chloro-5-(chloromethyl)pyridine, and
acetyl chloride.

In process (b), the compounds of the formula (IV) mean compounds based on the above definitions of Y and Z, preferably compounds based on the above preferred definitions.

The compounds of the formula (IV) can be obtained when 2-nitrominoimidazole is reacted with the compounds of the formula (III), in the presence of inert solvents.

The compounds of the formula (V) mean compounds based on the above definition of R, W and M.

In formula (V), R and W preferably have the preferred meanings as indicated above, while M preferably represents chlorine, bromine, iodine or tosyloxy.

The compounds of the formula (V) are known, and as examples thereof there may be mentioned:

2-chloro-5-(chloromethyl)pyridine,
2-chloro-5-(chloromethyl)thiazole,
5-chloromethyl-3-methyl-isoxazole, and
5-chloromethyl-2-methylpyridine.

In carrying out process (a) mentioned above, use may be made, as suitable diluent, of any inert solvents.

Examples of the solvents or diluents are water; aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, chlorobenzene and the like; ethers such as diethyl ether, methyl ethyl ether, di-isopropyl ether, dibutyl ether, propylene oxide, dioxane, tetrahydrofuran and the like; ketones such as acetone, methyl ethyl ketone, methyl isopropyl ketone, methyl isobutyl ketone and the like; nitriles such as acetonitrile, propionitrile, acrylonitrile and the like; alcohols such as methanol, ethanol, iso-propanol, butanol, ethylene glycol and the like; esters such as ethyl acetate, amyl acetate and the like; acid amides such as dimethyl formamide, dimethyl acetamide and the like; and sulfones and sulfoxides such as dimethyl sulfoxide, sulfolane and the like; and bases, for example, pyridine, etc.

Furthermore, use may be made, as the bases, of inorganic bases such as sodium hydroxide, potassium carbonate, sodium hydride and the like; and organic bases such as triethylamine and the like.

In process (a), the reaction temperature can be varied within a wide range. In general, the reaction is carried out at a temperature of about 0° to 120° C., preferably about 20°-80° C. In general, the reaction is allowed to proceed under normal pressure, although it is also possible to employ a higher or lower pressure.

When process (a) according to the invention is carried out, use is made, for instance, of about 1.0 to 1.2 moles of triethylamine as the base, and about 1 to 1.2 moles, preferably about 1 mole of the compound of the formula (III) per mole of the compound of the formula (II). The reaction may be conducted in the presence of an inert solvent such as dimethyl formamide to obtain the aimed compounds of the formula (I).

In carrying out process (a), furthermore it is possible first to convert the compound of formula (II) with a base such as sodium hydride into a sodium salt of the compound (II), which is then reacted with the compound of formula (III) to obtain the desired compound of formula (I).

When process (b) is carried out, it is possible to employ an inert solvent similar to that used in process (a) according to the invention.

Process (b) can be carried out under the same reaction conditions as those employed in process (a). When process (b) is conducted, for instance, use is made of about 1.0 to 1.2 moles of triethylamine as a base, and about 1 to 1.2 moles, preferably about 1 mole, of the compound of the formula (V) per mole of the compound of formula (IV). This reaction should preferably be carried out in the presence of inert solvents such as ethanol to yield the desired compounds of the formula (I).

The active compounds are well tolerated by plants, have a favorable level of toxicity to warm-blooded animals, and can be used for combating arthropod pests, espesically insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus Asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera; for example *Blatta orientalis, Periplaneta americana, Leucophaea maderae, Blattella germanica, Acheta domesticus,* Gryllotalpa spp., *Locusta migrato ria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci,* from the order of the Heteroptera, for example Eurygaster spp., *Dysdercus intermedius, Piesma guadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella auranti, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortix viridana;* from the order of the Coleoptera, for example *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilus, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-foaming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight.

The active compounds according to the invention can be presented in their commerically available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, and substances produced by microorganisms.

The active compounds according to the invention can furthermore be present in their commerically available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commerically available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and use of the active compounds according to the invention can be seen from the following examples.

EXAMPLES OF PREPARATION

Example 1

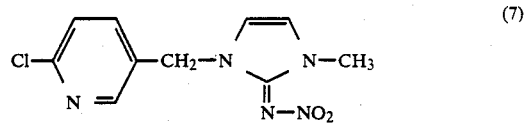
(7)

3H-1-(2-chloropyridin-5-yl-methyl)-2-nitroiminoimidazoline (5.1 g) was dissolved in dry dimethyl formamide (40 ml). To the resulting solution 60% sodium hydride in mineral oil (0.8 g) was incrementally added at a temperature of up to 10° C. After the completion of this addition, the reaction mixture was stirred at room temperature until the evolution of hydrogen had ceased. Thereafter, methyl iodide (3.4 g) was added to the mixture at the same temperature, and stirred at room temperature for 3 hours. After this reaction, the reaction mixture was poured into ice water. An extraction operation was carried out with the aid of dichloromethane. The dichloromethane layer was treated in a conventional manner, and the resulting residue was purified by means of a silica gel column chromatography, so that the desired compound, i.e. 1-(2-chloropyridin-5-yl-methyl)-3-methyl-2-nitroiminoimidazoline (3.0 g) was obtained. mp. 165°–167° C.

Example 2

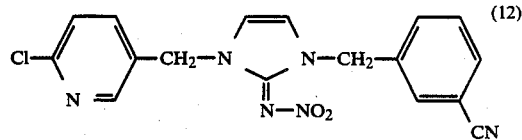
(12)

A mixture of 3H-1-(3-cyanobenzyl)-2-nitroiminoimidazoline (4.9 g), 2-chloro-5-chloromethylpyridine (3.2 g), triethylamine (2.2 g) and ethanol (40 ml) was refluxed under stirring for 3 hours. After the ethanol had been distilled off under a reduced pressure, the residue was mixed with dichloromethane, and the resulting mixture was washed with water and then with a 1% aqueous hydrochloric acid solution. After the dichloromethane layer had been treated in a conventional manner, the resultant residue was purified by means of a silica gel column chromatography, so that the desired compound, i.e. 1-(2-chloropyridin-5-yl-methyl)-3-(3-cyanobenzylmethyl)-2-nitroiminoimidazoline (0.7 g) was obtained. mp. 204°–206° C.

The compounds having the formula (I) of the present invention which can be prepared by the same processes as in Examples 1 or 2 are shown, together with the compounds of Examples 1 or 2, in the following Table 1.

TABLE 1

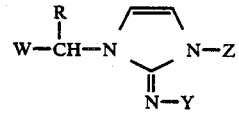

| Compound No. | R | Y | W | Z | mp., °C. |
|---|---|---|---|---|---|
| 1 | H | nitro | 3-pyridyl | methyl | |

TABLE 1-continued

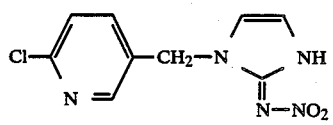

| Compound No. | R | Y | W | Z | mp., °C. |
|---|---|---|---|---|---|
| 2 | H | nitro | 3-pyridyl | n-butyl | |
| 3 | H | nitro | 3-pyridyl | 2-methylthioethyl | |
| 4 | H | nitro | 3-pyridyl | 2-cyanoethyl | |
| 5 | $CH_3$ | cyano | 3-pyridyl | acetyl | |
| 6 | H | nitro | 2-fluoropyridin-5-yl | allyl | |
| 7 | H | nitro | 2-chloropyridin-5-yl | methyl | 165–167 |
| 8 | H | cyano | 2-chloropyridin-5-yl | isopropyl | |
| 9 | H | nitro | 2-chloropyridin-5-yl | allyl | |
| 10 | H | nitro | 2-chloropyridin-5-yl | benzoyl | |
| 11 | H | nitro | 2-chloropyridin-5-yl | 4-chlorobenzyl | 196–198 |
| 12 | H | nitro | 2-chloropyridin-5-yl | 3-cyanobenzyl | 204–206 |
| 13 | H | nitro | 2,3-dichloropyridin-5-yl | methyl | |
| 14 | H | nitro | 2-methylpyridin-5-yl | 2-ethoxyethyl | |
| 15 | H | nitro | 3-methyl-isoxazol-5-yl | methyl | |
| 16 | H | cyano | 3-trifluoromethyl-isoxazol-5-yl | ethyl | |
| 17 | H | nitro | 1-methyl-pyrazol-4-yl | 3,4-dichloro-benzyl | |
| 18 | H | nitro | 1-isopropyl-pyrazol-4-yl | methyl | |
| 19 | H | nitro | 2-chloro-thiazol-5-yl | methyl | |
| 20 | H | nitro | 2-chloro-thiazol-5-yl | 3-chloro-allyl | |
| 21 | H | nitro | 1,2,5-thiadiazol-3-yl | methyl | |
| 22 | H | nitro | 2-methyl-pyrazin-5-yl | 4-chloro-benzyl | |
| 23 | H | nitro | 2-methyl-pyrimidin-5-yl | trichloroacetyl | |
| 24 | H | nitro | 2-chloro-pyridin-5-yl | 2-chloro-pyridin-5-yl-methyl | 164–166 |
| 25 | H | nitro | 2-chloro-thiazol-5-yl | 2-chloro-pyridin-5-yl-methyl | |
| 26 | H | nitro | 2-chloro-thiazol-5-yl | 2-chloro-thiazol-5-yl-methyl | |
| 27 | H | nitro | 3-methyl-isoxazol-5-yl | 3-chloro-pyridin-6-yl-methyl | |

Example 3 (Preparation of Intermediate Compound)

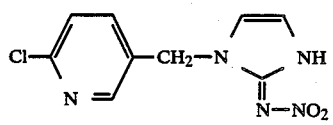

2-nitroaminoimidazole (12.8 g) was dissolved in dry dimethylformamide (100 ml). To the resultant solution 60% sodium hydride in mineral oil (4.8 g) was incrementally added at 5° C. After completion of this addition, the reaction mixture was stirred at room temperature until the evolution of hydrogen had ceased. Thereafter, a solution of 2-chloro-5-chloromethyl-pyridine (16.1 g) in dimethylformamide (20 ml) was added to the reaction mixture dropwise at a temperature of up to 10° C. Then the reaction mixture was stirred at room temperature for 3 hours. Thereafter, the reaction mixture was poured into ice water to precipitate the desired crystalline product. The product was separated by filtration, washed in ethanol and dried, so that the desired compound, i.e. 3H-1-(2-chloropyridin-5-yl-methyl)-2-nitroiminoimidazoline, (15.4 g) was obtained. mp. 186°–189° C.

According to the same procedure as shown above, by employing 3-cyanobenzyl chloride instead of 2-chloro-5-chloromethyl-pyridine. 3H-1-(3-cyanobenzyl)-2-nitroiminoimidazoline was obtained. mp. 193°–194° C. (decomposition).

Example 4 (Preparation of Intermediate Compound)

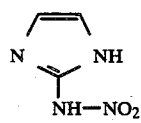

S-methyl-N-nitro-isothiourea (13.5 g) and aminoacetaldehyde dimethylacetal (10.5 g) were stirred together in methanol (150 ml) at 45° C. for 3 hours. After this reaction, the reaction mixture was admixed with 2N-HCl (40 ml), stirred at 60° C. for 4 hours, and then cooled.

The crystalline product thus formed was separated by filtration, washed in methanol and dried, so that the desired compound, i.e. 2-nitroaminoimidazole (9 g) was obtained. mp. 195°–200° C. (decomposition).

BIOTEST EXAMPLES

Comparative Compound

C-1:

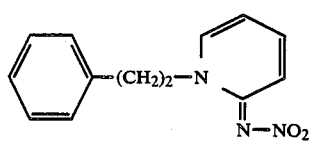

(disclosed in J. Med. Chem., vol. 14, pp. 988–990 (1971))

Example 5:

Biotest carried out against *Nephotettix cincticeps* exhibiting resistance to organophosphorus series insecticides Preparation of test formulation:
Solvent: 3 parts by weight of xylene
Emulsifier: 1 part by weight of polyoxyethylene-alkyl-phenyl-ether To prepare a suitable formulation of an active compound, 1 part by weight of the active compound was mixed with the above amount of the solvent containing the above amount of the emulsifier, and the mixture was diluted with water to the predetermined concentration.

Test Method:
Use was made of a plurality of pots each having a diameter of 12 cm in which were planted rice plant seedlings each having a height of about 10 cm.

Onto each potted rice-plant seedling were sprayed 10 ml of an aqueous solution of the active compound having the predetermined concentration.

After the sprayed solution was dried up, each of the pots was covered with a screen having a diameter of 7 cm and a height of 14 cm, in which 30 heads of female adults of *Nephotettix cincticeps* exhibiting resistance to organophosphorus-series insecticides were released, then each pot was placed in a constant temperature chamber. Two days after, the number of the killed insects was determined to obtain the mortality of insects.

In this test the compounds 7, 12 and 24 caused 100% insect mortality at a concentration of 40 ppm of the active ingredient whereas control C-1 was ineffective at said concentration.

Example 6

Biotest carried out against planthoppers
Test Method:
Use was made of a plurality of pots each having a diameter of 12 cm in which were planted rice plant seedlings each having a height of about 10 cm.

Onto each potted rice-plant seedling were sprayed 10 ml of an aqueous solution of the active compound having the predetermined concentration, which had been prepared according to a procedure similar to Example 5.

After the sprayed solution was dried up, each of the pots was covered with a screen having a diameter of 7 cm and a height of 14 cm, in which 30 heads of female adults of *Nilaparvata lugens* exhibiting resistance to organophosphorus-series insecticides were released, then each pot was placed in a constant temperature chamber. Two days after, the number of the killed insects was determined to obtain the mortality of insects.

In a similar manner, tests were made on *Sogatella furcifera* and *Laodelphax striatellus* exhibiting resistance to organophosphorus-series insecticides, to obtain the insect mortality.

In this test the compounds 12 and 24 caused 100% insect mortality against *Nilaparvata lugens, Laodelphax striatellus* and *Sogatella furcifero* at a concentration of 200 ppm of the active ingredient whereas control C-1 was ineffective at said concentration.

Example 7

Biotest carried out against *Myzus persicae* exhibiting resistance to organophosphorus and carbamate-series insecticides
Test Method:

Onto eggplant seedlings (black long eggplant) each having a height of 20 cm and planted in an unglazed pot having a diameter of 15 cm were inoculated, per seedling, 200 heads of grown *Myzus persicae* having resistance against organophosphorus and carbamate-series insecticides. One day after the inoculation, an aqueous solution having a predetermined concentration of the active compound, which had been prepared according to a procedure similar to Example 5, was sprayed onto the seedlings with a sufficient dosage by means of a spray gun.

The above-mentioned test was carried out for each of the below-indicated active compounds with the indicated concentration dosages. After the spraying of the insecticidal solution, the seedlings in the pot for each test were allowed to stand for 24 hours in a green house kept at a temperature of 28° C. and, thereafter, the death rate of the insects was determined for each test. The same test was repeated twice for the purpose of obtaining accurate death rate determinations. In this test the compounds 7 and 24 caused 100% insect mortality at a concentration of 200 ppm of the active ingredient, whereas control C-1 was ineffective even at a concentration of 1000 ppm!

It will be appreciated that the instant specification and claims are set forth by way of illustration and not limitation, and that various modifications and changes may be made without departing from the spirit and scope of the present invention.

We claim:

1. A compound of the formula

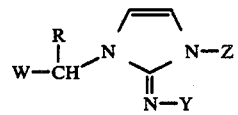

in which
R is hydrogen or methyl,
Y is nitro or cyano,
W is an aromatic 5- or 6-membered heterocyclic group having one nitrogen hetero-atom and optionally a second hetero atom selected from the group consisting of nitrogen, oxygen and sulfur, the heterocyclic group radical optionally being substituted by at least one substituent selected from the group consisting of halogen, alkyl with 1 to 4 carbon atoms, alkoxy with 1 to 4 carbon atoms, haloalkyl with 1 to 4 carbon atoms, haloalkoxy with 1 to 4 carbon atoms, alkenyl with 2 to 4 carbon atoms, alkylthio with 1 to 4 carbon atoms, alkylsulfinyl with 1 to 4 carbon atoms, alkylsulfonyl with 1 to 4 carbon atoms, and alkynyl with 3 to 4 carbon atoms, and
Z is alkyl with 1 to 4 carbon atoms, alkenyl with 3 carbon atoms, alkynyl with 3 carbon atoms, alkoxyalkyl with 2 to 4 carbon atoms in total, alkylthioalkyl with 2 to 4 carbon atoms in total, cyano-substituted alkyl with 1 to 2 carbon atoms, chloroalkenyl with 3 carbon atoms, benzyl (which may optionally be substituted with chlorine or cyano), acetyl (which may optionally be substituted by chlorine), benzoyl or —CH₂—W.

2. A compound according to claim 1, in which
R is hydrogen,
Y is nitro,
W is pyridyl or thiazolyl optionally substituted by chlorine, methyl or trifluoromethyl, and Z is methyl, allyl, propargyl, 3-cyanobenzyl, 4-chlorobenzyl, acetyl, benzoyl, 2-chloro-5-pyridyl or 2-chloro-5-thiazolyl.

3. An imidazoline according to claim 1, wherein such compound is 1-(2-chloropyridin-5-yl-methyl)-3-methyl-2-nitroiminoimidazoline of the formula

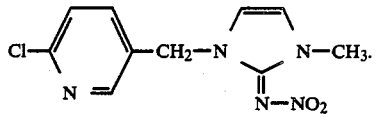

4. An imidazoline according to claim 1, wherein such compound is 1-(2-chloropyridin-5-yl-methyl)-3-(3-cyanobenzyl)-2-nitroiminoimidazoline of the formula

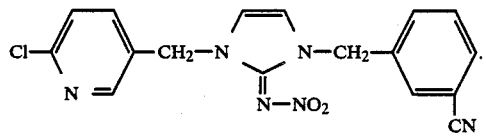

5. An imidazoline according to claim 1, wherein such compound is 1,3-bis-(2-chloropyridin-5-yl-methyl)-2-nitroiminoimidazoline of the formula

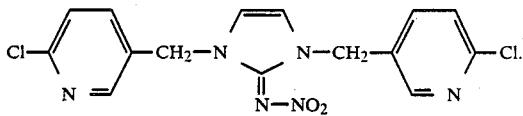

6. An insecticidal composition comprising an insecticidally effective amount of a compound according to claim 1 and a diluent.

7. A method of combating insects which comprises applying to such insects or to an insect habitat an insecticidally effective amount of a compound according to claim 1.

8. The method according to claim 7, wherein such compound is
1-(2-chloropyridin-5-yl-methyl)-3-methyl-2-nitroiminoimidazoline,
1-(2-chloropyridin-5-yl-methyl)-3-(3-cyanobenzyl)-2-nitroiminoimidazoline or
1,3-bis-(2-chloropyridin-5-yl-methyl)-2-nitroiminoimidazoline.

* * * * *